US012603180B2

(12) United States Patent
Seong

(10) Patent No.: US 12,603,180 B2
(45) Date of Patent: Apr. 14, 2026

(54) METHOD, APPARATUS, AND COMPUTER PROGRAM FOR PROVIDING PRECOCIOUS PUBERTY PREDICTION AND SOLUTION FOR EACH GROWTH STAGE USING ARTIFICIAL INTELLIGENCE

(71) Applicant: GP CO., LTD., Gwangmyeong-si (KR)

(72) Inventor: Je Hyeok Seong, Gwangmyeong-si (KR)

(73) Assignee: GP CO., LTD., Gwangmyeong-si (KR)

( * ) Notice: Subject to any disclaimer, the term of this patent is extended or adjusted under 35 U.S.C. 154(b) by 78 days.

(21) Appl. No.: 18/572,301

(22) PCT Filed: Jul. 6, 2023

(86) PCT No.: PCT/KR2023/009549

§ 371 (c)(1),
(2) Date: Dec. 20, 2023

(87) PCT Pub. No.: WO2024/071602

PCT Pub. Date: Apr. 4, 2024

(65) Prior Publication Data

US 2025/0087353 A1     Mar. 13, 2025

(30) Foreign Application Priority Data

Sep. 29, 2022    (KR) ......................... 10-2022-0124098

(51) Int. Cl.
*G16H 50/20*        (2018.01)
*G16H 10/60*        (2018.01)
(52) U.S. Cl.
CPC ............. *G16H 50/20* (2018.01); *G16H 10/60* (2018.01)
(58) Field of Classification Search
None
See application file for complete search history.

(56) References Cited

U.S. PATENT DOCUMENTS

2017/0354351 A1* 12/2017 Krans ..................... G16H 20/60
2021/0142477 A1*  5/2021 Tsai ....................... G06T 7/0012
(Continued)

FOREIGN PATENT DOCUMENTS

CN        111553412 A  *  8/2020  ........... G06F 18/241
CN        114936320 A  *  8/2022
(Continued)

OTHER PUBLICATIONS

Pan L, Liu G, Mao X, Li H, Zhang J, Liang H, Li X. Development of Prediction Models Using Machine Learning Algorithms for Girls with Suspected Central Precocious Puberty: Retrospective Study. JMIR Med Inform. Feb. 12, 2019;7(1) (Year: 2019).*
(Continued)

*Primary Examiner* — Jonathan Ng
(74) *Attorney, Agent, or Firm* — WHDA, LLP

(57) ABSTRACT

The present invention relates to a method, apparatus, and computer program for predicting precocious puberty for each stage of growing children and adolescents using an artificial intelligence model. The method for providing precocious puberty prediction and solution for each growth stage using artificial intelligence includes: receiving time series physical information on an evaluation subject; classifying a plurality of growth stages based on the input physical information on the evaluation subject, and then extracting physical information corresponding to a normal growth stage among the plurality of growth stages; predicting precocious puberty by inputting the extracted physical information to a trained neural network; and providing a precocious puberty management solution based on the physical information on the evaluation subject when the evaluation subject corresponds to the precocious puberty.

14 Claims, 7 Drawing Sheets

(56)    References Cited

U.S. PATENT DOCUMENTS

| | | | | |
|---|---|---|---|---|
| 2022/0202351 A1* | 6/2022 | Neumann | .............. | G16H 50/30 |
| 2024/0177628 A1* | 5/2024 | Han | ....................... | G09B 23/28 |

FOREIGN PATENT DOCUMENTS

| | | | | | |
|---|---|---|---|---|---|
| CN | 119517429 A | * | 2/2025 | ............ | G06N 20/20 |
| JP | 2020-38573 A | | 3/2020 | | |
| KR | 10-2014-0045759 A | | 4/2014 | | |
| KR | 10-1779800 | * | 9/2017 | | |
| KR | 10-1779800 B1 | | 9/2017 | | |
| KR | 10-1866208 B1 | | 6/2018 | | |
| KR | 20200031912 A | * | 9/2018 | | |
| KR | 10-2019-0072292 A | | 6/2019 | | |
| KR | 10-2075743 B1 | | 2/2020 | | |
| KR | 10-2198302 B1 | | 1/2021 | | |
| KR | 10-2022-0007030 A | | 1/2022 | | |
| WO | WO-2018078653 A1 | * | 5/2018 | .............. | G06F 9/44 |
| WO | WO-2024172329 A1 | * | 8/2024 | ............ | G06N 3/045 |

OTHER PUBLICATIONS

International Search Report dated Nov. 2, 2023, issued in counterpart International Application No. PCT/KR2023/009549. (3 pages).

* cited by examiner 50-1

13

START

INPUT PHYSICAL INFORMATION ON EVALUATION SUBJECT —S100

CLASSIFY GROWTH STAGE —S310

EXTRACT PHYSICAL INFORMATION —S330

PREDICT PRECOCIOUS PUBERTY —S350

GENERATE PRECOCIOUS PUBERTY MANAGEMENT SOLUTION —S370

DISPLAY SOLUTION —S390

END

METHOD, APPARATUS, AND COMPUTER PROGRAM FOR PROVIDING PRECOCIOUS PUBERTY PREDICTION AND SOLUTION FOR EACH GROWTH STAGE USING ARTIFICIAL INTELLIGENCE

TECHNICAL FIELD

The present invention relates to a method, apparatus, and computer program for predicting precocious puberty for each grow stage of growing children and adolescents using an artificial intelligence model.

BACKGROUND ART

With the recent development of artificial intelligence technologies, the artificial intelligence technologies are being applied to various fields. Instead of existing data processing methods, methods of generating additional information by extracting features inherent in data through neural network models have been developed and used.

The neural network model used for artificial intelligence may detect and recognize features within input data more quickly and accurately through learning than general data processing. Recently, the artificial intelligence technology has gone beyond simply tracking and detecting objects and is also being applied to train a past history and derive current features that reflect future predictions or time series change information.

Among these, the predictive analysis is a technology in areas of statistics and data mining that extracts information from data and uses the extracted information to predict trends, behavior patterns, etc. This predictive analysis may be applied to all areas where decisions are needed based on information obtained from data. The core of predictive analysis is understanding the relationships between variables and then predicting unknown variables.

For this purpose, various approaches are being used depending on the data characteristics and prediction target.

Among various fields that require the predictive analysis, there is the field of physical growth in children and adolescents. There is a lot of interest among parents and children and adolescents about when and how much children and adolescents will grow taller or whether there is a risk of developing precocious puberty, obesity, etc., that may accompany the growth of children and adolescents.

Regarding the conventional prediction of height growth, a method for predicting a growth plate by taking an X-ray or analyzing a relationship with genetic/environmental factors has been proposed (Korean Patent Publication No. 10-2075743, Korean Patent Publication No. 10-1866208), and a method for making physical data of sample subjects having different measurement times or number of measurements into a form suitable for training a growth prediction model has been proposed (Korean Patent Publication No. 10-2198302).

Conventionally, the methods for predicting physical growth of children and adolescents have been proposed, but as described above, research on methods for predicting and providing solutions for a risk of occurrence of precocious puberty and obesity that may accompany the growth of children and adolescents is insufficient.

In addition, since the children and adolescents have growth stages with different features, it is possible to increase the reliability of providing solutions through predicted data and analysis by considering the growth stages.

RELATED ART DOCUMENT

Patent Document (Patent Document 001) Korean Patent Publication No. 10-2075743
(Patent Document 002) Korean Patent Publication No. 10-1866208
(Patent Document 003) Korean Patent Publication No. 10-2198302

DISCLOSURE

Technical Problem

Accordingly, an object of the present invention is to solve the above problems.

One of various problems of the present invention provides a method, apparatus, and computer program capable of predicting precocious puberty for each stage of children and adolescents with a high risk of developing precocious puberty using a prediction model generated through artificial intelligence learning, and providing customized solutions.

Technical Solution

In an aspect of the present invention, a method for providing precocious puberty prediction and solution for each growth stage using artificial intelligence includes: receiving time series physical information on an evaluation subject; classifying a plurality of growth stages based on the input physical information on the evaluation subject, and then extracting physical information corresponding to a normal growth stage among the plurality of growth stages; predicting precocious puberty by inputting the extracted physical information to a trained neural network; and providing an precocious puberty management solution based on the physical information on the evaluation subject when the evaluation subject corresponds to the precocious puberty.

The method may further include, after the receiving of the physical information on the evaluation subject, classifying the gender of the evaluation subject.

A period of the normal growth stage may be set differently based on the gender of the evaluation subject.

The neural network may perform multi-modal learning using different types of training data.

The neural network may include a first model that trains physical information corresponding to a normal growth stage among a plurality of growth stages as training data based on the time series physical information on the plurality of sample subjects.

The neural network may further include a second model trained using bone maturity data of the evaluation subject as the training data.

In another aspect of the present invention, there is provided a program stored in a computer-readable recording medium including a program code for executing the method for providing precocious puberty prediction and solution for each growth stage using artificial intelligence described above.

In another aspect of the present invention, there is provided a computer-readable recording medium in which a program for executing the method for providing precocious puberty prediction and solution for each growth stage using artificial intelligence described above is recorded.

In another aspect of the present invention, an apparatus for providing precocious puberty prediction and solution for each growth stage using artificial intelligence includes: an input unit configured to receive time series physical information on an evaluation subject; a growth stage determination unit configured to classify a plurality of growth stages based on the physical information on the evaluation subject input to the input unit, and then extracting physical information corresponding to a normal growth stage among the plurality of growth stages; a precocious puberty prediction unit configured to predict the precocious puberty by inputting the extracted physical information to a trained neural network; a solution generation unit configured to generate a precocious puberty management solution based on the physical information on the evaluation subject when the evaluation subject corresponds to the precocious puberty; and a display unit configured to display the generated precocious puberty management solution.

The apparatus may further include: a gender determination unit configured to classify a gender of the evaluation subject input to the input unit, in which the solution generation unit may generate a precocious puberty management solution differently depending on the gender of the evaluation subject.

The growth stage determination unit may extract the physical information by setting a period of the normal growth stage differently based on the gender of the evaluation subject to extract physical information.

The neural network may perform multi-modal learning using different types of training data.

The neural network may include a first model that trains physical information corresponding to a normal growth stage among a plurality of growth stages as training data based on the time series physical information on the plurality of sample subjects.

The neural network may further include a second model trained using bone maturity data of the evaluation subject as the training data.

Each feature of the above-described embodiments may be implemented in combination in other embodiments unless inconsistent with or exclusive of the other embodiments.

Advantageous Effects

According to various embodiments of the present invention, it is possible to accurately predict precocious puberty by considering a growth stage of children and adolescents through a prediction model generated through artificial intelligence learning, and provide solutions necessary to prevent the precocious puberty based on the accurate growth stage of the children and adolescents.

The effects of the present invention are not limited to the above-mentioned effects, and other effects that are not mentioned may be obviously understood by those skilled in the art from the following description.

BEST MODEL

Figure 1:
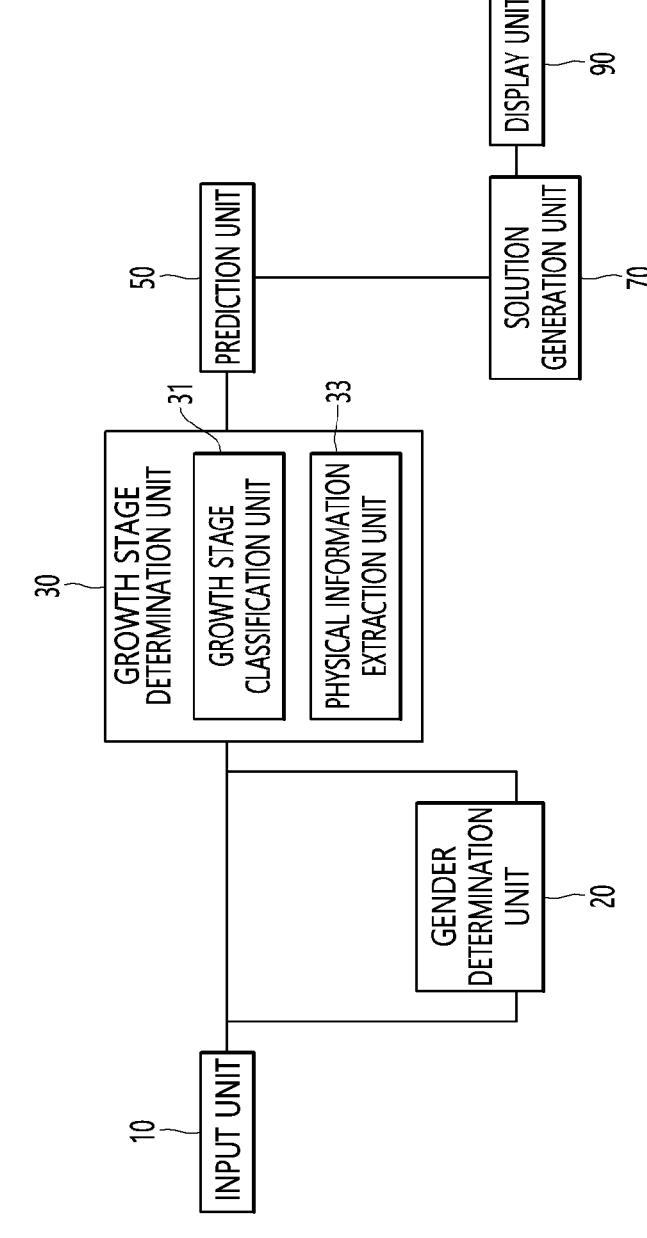
FIG. 1 is a diagram illustrating a system for providing precocious puberty prediction and solution for each growth stage according to an exemplary embodiment of the present invention.

Hereinafter, detailed embodiments of the present invention will be described with reference to the accompanying drawings. The following detailed descriptions are provided to help a comprehensive understanding of methods, devices and/or systems described herein. However, the embodiments are described by way of examples only and the present invention is not limited thereto.

In describing the embodiments of the present invention, when a detailed description of well-known technology relating to the present invention may unnecessarily make unclear the spirit of the present invention, a detailed description thereof will be omitted. Further, the following terminologies are defined in consideration of the functions in the present invention and may be construed in different ways by the intention, practice, etc., of users and operators. Therefore, the definitions thereof should be construed based on the contents throughout the specification. The terms used in the detailed description is merely for describing the embodiments of the present invention and should in no way be limited. Unless clearly used otherwise, an expression in the singular form includes the meaning of the plural form. In this description, expressions such as "including" or "comprising" are intended to indicate certain characteristics, numbers, steps, operations, elements, some or combinations thereof, and it should not be interpreted to exclude the existence or possibility of one or more other characteristics, numbers, steps, operations, elements, parts or combinations thereof other than those described.

In addition, terms 'first', 'second', A, B, (a), (b), and the like, will be used in describing components of embodiments of the present invention. These terms are used only in order to distinguish any component from other components, and features, sequences, or the like, of corresponding components are not limited by these terms.

In an exemplary embodiment of the present invention, children and adolescents may be understood as a concept that includes a growth period of a human body. In more detail, the children and adolescents meaning evaluation subjects in exemplary embodiments of the present invention are defined below through the meanings of toddlers, children, adolescents, infants, and young children.

The toddlers are a continuation of a neonatal period and grow by biting on their mother's nipples for up to 2 years after birth. During this period, all experiences of nutrition, caress, and excretion affect general tendencies later in life. The children usually refer to persons between the age of 6 and the age of 13, and in a broad sense, may include infants (the ages of 1 to 5).

The adolescents are an intermediate period between children and young adults, and generally refer to persons between 13 years old and 19 years old based on age. The infants may refer to from 1 year old to the ages of 1 to 5. The young children may generally refer to children up to the age of 15.

Therefore, in a narrow sense, the children and adolescents meaning the evaluation subject, may refer to a period between the ages of 5 and 19, including children and adolescents, and in a broad sense, may refer to a period that encompasses all normal periods in which physical growth occurs, including a period from a toddler period to an adolescent period.

Figure 2:
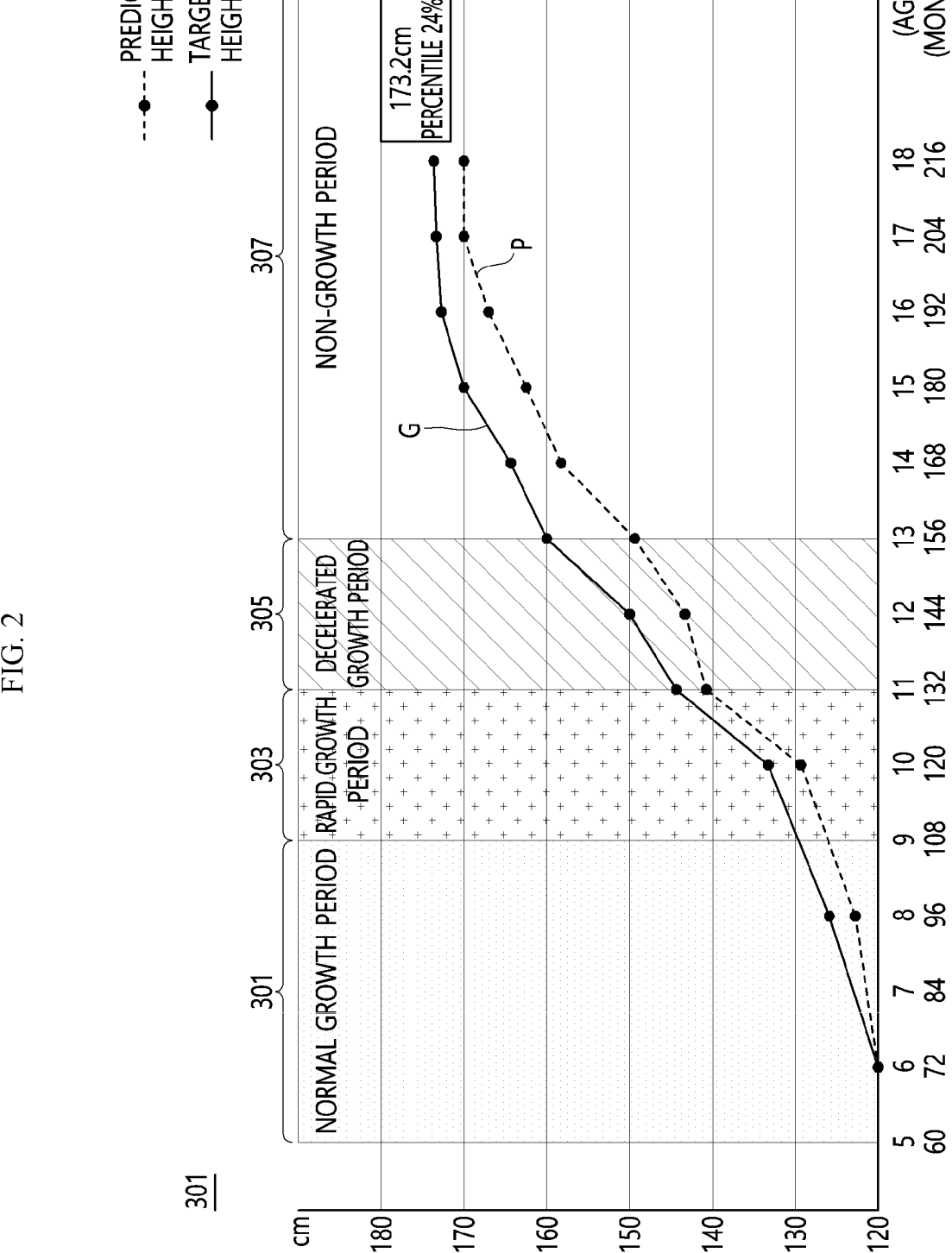
FIG. 2 is a diagram illustrating a predicted height and targeted height in the case of precocious puberty for each growth stage according to an exemplary embodiment of the present invention.

FIG. 1 is a diagram illustrating a system for providing precocious puberty prediction and solution for each growth stage according to an exemplary embodiment of the present invention, and FIG. 2 is a diagram illustrating predicted heights and targeted heights for each growth stage according to an exemplary embodiment of the present invention.

It will be described with reference to FIGS. 1 and 2 below.

A system for providing precocious puberty prediction and solution for each growth stage according to an exemplary embodiment of the present invention includes an input unit 10, a gender determination unit 20, a growth stage determination unit 30, a prediction unit 50, a solution generation unit 70, and a display unit 90.

The system may receive time series physical information on an evaluation subject through the input unit 10. The physical information on the evaluation subject may not only include basic information such as grade (or age), gender, and height, but also additional information such as body weight, protein, mineral content, body fat, body water, soft lean mass, fat free mass, bone tissue, skeletal muscle mass, body mass index (BMI), basal metabolic rate, neck circumference, chest circumference, abdominal circumference, thigh circumference, arm circumference, hip circumference, etc. This physical information is only an example to help understand the present invention, and the present embodiment is not limited thereto. Of course, the types of information constituting the physical information may be changed in various ways according to the embodiment.

The time series physical information on the evaluation subject may be continuous information or discontinuous information, but may be information included in at least one of periods corresponding to growth stages in FIG. 2.

More specifically, the collection time and the number of collections of the time series physical information on the evaluation subject are various. For example, in the case of a first evaluation subject, there may be physical information measured from 8 to 12 years old, which is part of the children and adolescents period, and in the case of a second evaluation subject, there may be physical information measured irregularly, such as 8, 10 to 12, and 15 years old. In addition, in the case of a third evaluation subject, there may be physical information measured multiple times within a certain period of time (within the period of any one of the plurality of growth stages in FIG. 2), whereas in the case of a fourth evaluation subject, there may be physical information that is measured only once within a certain period of time (within the period of any one of the plurality of growth stages in FIG. 2).

As described above, depending on the collection time and number of times of collection, the physical information on the evaluation subject may be included in two or more of the growth stages in FIG. 2 (the first evaluation subject and the second evaluation subject), but may not be included therein (the third evaluation subject and the fourth evaluation subject).

Like the third evaluation subject above, when there is physical information measured multiple times within one of the plurality of growth stages, the growth stage determination unit 30 may classify the growth stage to which the physical information on the third evaluation subject corresponds through a growth stage classification unit 31, and extract physical information through a physical information extraction unit 33. Here, the extracted physical information may generally include the physical information on all the evaluation subjects input through the input unit 10.

However, like the fourth evaluation subject, when the physical information on the evaluation subject corresponds to only one of the plurality of growth stages and is the physical information measured only once within the period, before the physical information on the evaluation subject is input to the growth stage determination unit 30, the corresponding physical information may be additionally generated within an arbitrary period.

More specifically, the time series physical information on the evaluation subject corresponding to an arbitrary period may be generated based on the input physical information on the evaluation subject and pre-stored time series physical growth information on a plurality of sample subjects.

As an example, the physical information may be generated based on a distribution model (similarity) between the input physical information on the evaluation subject and the pre-stored time series physical growth information on the plurality of sample subjects, or the physical information may be generated based on a Bayesian inference model (conditional probability).

The growth stage determination unit 30 may perform classification into one of the plurality of growth stages in the growth stage classification unit 31 based on the physical information on the evaluation subject input through the input unit 10, and the physical information extraction unit 33 may extract the physical information corresponding to the classified growth stage.

Looking at the growth stage with reference to FIG. 2, the children and adolescents period may include a normal growth period 301, a rapid growth period 303, a decelerated growth period 305, and a non-growth period 307.

Each growth stage may be classified according to the growth rate, and a height growing each year varies depending on each growth stage, and even in the same growth stage, the actual growing height may vary depending on the growth type.

The normal growth period 301 generally refers to the period before puberty when secondary sexual characteristics appear. The children and adolescents corresponding to this period generally have open growth plates. As a result, depending on the growth environment, in the case of a short height growth type, a height generally grows by 4 to 5 cm per year, and in the case of a tall growth type, a height grows in the range of 6 to 7 cm per year.

The rapid growth period 303 is a period in which secondary sexual characteristics begin to appear. In women, a breast swells and a lump appears, and in men, the testicles grow larger, pubic hair begins to grow, and a voice break appears where voice changes. The rapid growth period 303 generally lasts about 2 to 3 years after the normal growth period 301, and a height grows in the range of 7 to 10 cm per year on average.

The decelerated growth period 305 refers to a period in which the secondary sexual characteristics are completed. During this period, in the case of women, the secondary sexual characteristics may be clearly identified starting from menarche, and in the case of men, the secondary sexual characteristics may be clearly identified through pubic hair, voice change, and armpit hair. In the decelerated growth period 305, the growth rate drops rapidly compared to the rapid growth period 303. The decelerated growth period 305 generally lasts about 2 to 3 years, and a height grows in the range of 5 to 6 cm per year on average, and does not naturally grow any further. The growth plate begins to close little by little after the rapid growth period 304, and closes approximately 50% about 6 months after entering the decelerated growth period 305.

The non-growth period 307 refers to a period in which the growth plate has closed, as a period in which the growth period has not completely ended but natural height growth has become difficult. Generally, women enter the non-growth period 307 about 1 year and 6 months to 2 years after menarche, and men enter the non-growth period 307 about 1 year and 6 months to 2 years from the time hair begins to appear in armpits. In the non-growth period 307, the growth plate closes and the natural growth stops, but by changing bad lifestyle habits and improving a physical function through customized exercise, posture correction, and nutrient intake, etc., a height may grow in the range of about 1 to 3 cm.

In FIG. 2, an x-axis represents age and months, and a y-axis represents height (cm). Relatively, an upper solid line P represents a predicted growth rate of an evaluation subject, and a lower dotted line G represents a targeted growth rate of an evaluation subject.

The precocious puberty is generally considered to occur when in girls, breasts or pubic hair appear before 8 year old, or in boys, pubic hair appears, the penis enlarges, or the testicles enlarge to more than 4 mL before 9 years old.

During normal puberty in girls, hypothalamic-pituitary activation occurs first, followed by secretion of female hormones from the ovaries, breasts appear, and other physical changes (development of pubic hair, rapid height growth, acne) appear sequentially.

During normal puberty in boys, after hypothalamic-pituitary activation occurs first, as the testicles grow, secretion of male hormones increases, and other physical changes (development of pubic hair, rapid height growth, acne) appear sequentially.

There are various causes of the precocious puberty, but in general, sex hormones are secreted at an early age and affect the body, resulting in a rapid growth rate (for example, height growth). This type of precocious puberty is more common in girls than boys, but cases with serious pathological causes are more common in boys.

More specifically, a distribution appears in which, in girls, idiopathic, where precocious puberty occurs without any underlying disease, is the most common at 80%, ovarian tumors account for 15%, and cerebral lesions account for about 5%, and in boys, idiopathic without any underlying disease accounts for 50%, a case where lesions are in a cerebrum itself accounts for 20%, adrenal cortical hyperplasia or tumors account for 25%, and testicular tumors are 5%, etc. This distribution varies depending on the age of occurrence.

In summary, the precocious puberty may be understood as a group of physical change diseases caused by a wide variety of causes. Generally, it occurs in both boys and girls during the normal growth period 301 in FIG. 2. During this period, there is a rapid growth rate and it occurs more commonly in girls than in boys, but boys are more likely to have serious pathological causes.

Therefore, in this embodiment, in order to more accurately provide precocious puberty prediction and solution based on the growth stage, gender may be classified through the gender determination unit 20 based on the physical information on the evaluation subject input through the input unit 10, and then the growth stage may be classified in the growth stage determination unit 30 based on the classified gender, and the physical information corresponding to the normal growth stage among the classified growth stages may be extracted, and then a solution may be generated in the solution generation unit 70 by considering the gender of the evaluation subject.

The prediction unit 50 is a type of prediction model and may be implemented with artificial intelligence in a recursive neural network (RNN) structure so that it may use not only current values but also time series values. For example, the prediction model may be implemented with architecture such as Long Short Term Memory (LSTM) or Gated Recurrent Units (GRU) that is the RNN. Of course, in addition to this, conventional various artificial intelligence architectures may be applied to the prediction model of this embodiment, which will be described in detail with reference to FIGS. 3 to 5 described later.

The solution generation unit 70 may generate a precocious puberty management solution for the evaluation subject according to the classified growth stage.

In other words, the prediction of the precocious puberty may be performed based on the physical information corresponding to the normal growth period 301 among the plurality of growth stages based on the time series physical information on the evaluation subject, and the management solution for precocious puberty may be provided in a manner of lowering the growth rate in the plurality of growth stages.

More specifically, when the evaluation subject corresponds to the normal growth period 301, a solution for reducing the growth prediction value P of the evaluation subject may be provided. The growth prediction value P is a value corresponding to the y-axis in FIG. 2, and the solution for reducing the growth prediction value P may be provided to the evaluation subject through various solution display units 90 for the expected target value G of the y-axis.

Examples of the solutions provided through the display unit 90 may include current height, predicted height, obesity level, body fat mass, skeletal muscle mass, protein mass, mineral mass, sleep amount, exercise amount, nutritional information, lifestyle habits, posture, etc. Each indicator may be expressed step by step as caution, normal, good, etc., based on a preset range, or may also be expressed as a level.

Additionally, the current state, customized solutions, precautions, etc., for each indicator may be displayed. The current state may be displayed step by step or level based on the target value G. The customized solution may include contents for adjustment of protein, mineral content, body fat, body water, soft lean mass, fat free mass, bone tissue, skeletal muscle mass, body mass index (BMI), basal metabolic rate, etc., to reach the current target value G based on the input physical information.

The precautions may include contents for adjustment of the current insufficient amount of protein, mineral content, body fat, body water, soft lean mass, fat free mass, bone tissue, skeletal muscle mass, body mass index (BMI), basal metabolic rate, etc., based on the input physical information.

In addition, when the evaluation subject corresponds to the rapid growth period 303, a solution for reducing the period of the rapid growth period 303 of the evaluation subject may be provided.

This reduces the period of the rapid growth period 303. The rapid growth period 303 generally begins when secondary sexual characteristics begin to appear. As described above, it may be defined as a period that ends when secondary sexual characteristics are completed. However, when the evaluation subject is determined to be the precocious puberty through the prediction unit 50, the evaluation subject is a case in which the secondary sexual characteristics have already begun in the normal growth period 301, and a solution for advancing the completion time of the secondary sexual characteristics may be provided. In other words, various solutions for narrowing the range of the x-axis corresponding to the rapid growth period 303 in FIG. 2 may be provided to the evaluation subject through the display unit 90.

This may slow down the degree of progress of the precocious puberty by reducing the height increase rate. However, when the height increase rate is reduced too much, the increase in the final adult height may not be evident, so the target value G may be trained to be set within a predetermined range based on the value P predicted by the precocious puberty.

When the above-described evaluation subject corresponds to the normal growth period 301, it may include, especially, contents on adjustment of indicators that may alleviate abnormal increases in sex hormones, including the physical information to be considered.

In addition, when the evaluation subject corresponds to the decelerated growth period 305, a solution for controlling the period of the decelerated growth period 305 of the evaluation subject may be provided. The growth stage period adjustment may be divided into the case where the physical information on the evaluation subject is located at the beginning of the decelerated growth period 305 and the case where the physical information on the evaluation subject is located at the mid to late part of the decelerated growth period 305, among the growth stages classified based on the input physical information on the evaluation subject.

The standard for distinguishing between the beginning and the mid to late parts of the above-mentioned decelerated growth period 305 may be divided based on a predetermined range corresponding to the decelerated growth period 305 from the rapid growth period 303 with respect to the x-axis in FIG. 2. Alternatively, based on whether the secondary sexual characteristics are completed based on the input physical information on the evaluation subject, when the secondary sexual characteristics are not completed, it may be classified as the beginning of decelerated growth period 305, and when the secondary sexual characteristics are completed, it may be divided as the mid to late part of the decelerated growth period 305.

Preferably, it is possible to determine whether the secondary sexual characteristics have been completed based on the input physical information on the evaluation subject to determine whether the current physical information on the evaluation subject is located at the beginning or mid to late part of the decelerated growth period 305, and when it is not possible to determine whether the secondary sexual characteristics have been completed based on the input physical information on the evaluation subject, it is possible to determine whether the physical information on the evaluation subject is located at the beginning or mid to late part of the decelerated growth period 305 based on the predetermined range corresponding to the decelerated growth period 305 from the rapid growth period 303.

Meanwhile, when the input physical information on the evaluation subject is located at the beginning of the decelerated growth period 305, a period adjustment solution for advance the entry into the decelerated growth period 305 may be provided. As described above, the secondary sex characteristics are being completed when transitioning from the rapid growth period 303 to the decelerated growth period 305, so it is possible to provide a solution for advancing the time when the secondary growth is completed. This may be similar to the solution provided when the evaluation subject corresponds to the rapid growth period 303. In other words, various solutions for moving the range of the x-axis corresponding to the decelerated growth period 305 in FIG. 2 to the left may be provided to the evaluation subject through the display unit 90. In this case, the range of decelerated growth period 305 may increase depending on the physical information on the evaluation subject, or may decrease as the rapid growth period 303 increases.

Meanwhile, when the input physical information on the evaluation subject is located at the mid to late part of the decelerated growth period 305, the period adjustment solution for increasing the entry into the decelerated growth period 305 may be provided. As described above, the mid to late part of the decelerated growth period 305 generally refers to the period when the growth plate of the evaluation subject is closed after the secondary sexual characteristics are completed. Generally, about 50% of the growth plate closes 6 months after entering the decelerated growth period 305, and when the growth plate closes and the natural growth stops, the non-growth period 307 is entered. In this case, a solution for increasing the period of decelerated growth period 305 may be provided. In other words, various solutions for widening the range of the x-axis corresponding to the decelerated growth period 305 in FIG. 2 to the left may be provided to the evaluation subject through the display unit 90.

When the above-described evaluation subject corresponds to the normal growth period 301, it may include, especially, contents on adjustment of indicators that may alleviate the degree that the growth plate closes, including the physical information to be considered.

Accordingly, as described above, in the case of the precocious puberty, the secondary sexual characteristics are generally in progress starting from normal growth period 301, and there is a need to lower the growth rate in the normal growth period 301 and the rapid growth period 303, but since the increase in the final adult height may not be evident, after the secondary growth characteristics are completed, it is necessary to increase the growth rate again in the mid to late part of the decelerated growth period 303 and the non-growth period 307 to be described below.

Therefore, when the evaluation subject corresponds to the non-growth period 307, a solution for improving physical functions through lifestyle habits, customized exercise, posture correction, nutrient intake, etc., based on the input physical information on the evaluation subject may be provided.

In the non-growth period 307, the growth plate closes and the natural growth stops, so the solutions for improving the physical functions through the lifestyle habits, the customized exercise, the posture correction, etc., based on body weight, body fat, body water, soft lean mass, skeletal muscle mass, body mass index (BMI), basal metabolic rate, neck circumference, chest circumference, abdominal circumference, thigh circumference, arm circumference, and hip circumference, etc., of the evaluation subject may be provided or the solution for improving the physical functions through the nutrient intake, etc., based on protein, mineral content, bone tissue (bone density), etc., may be provided.

Figure 3:
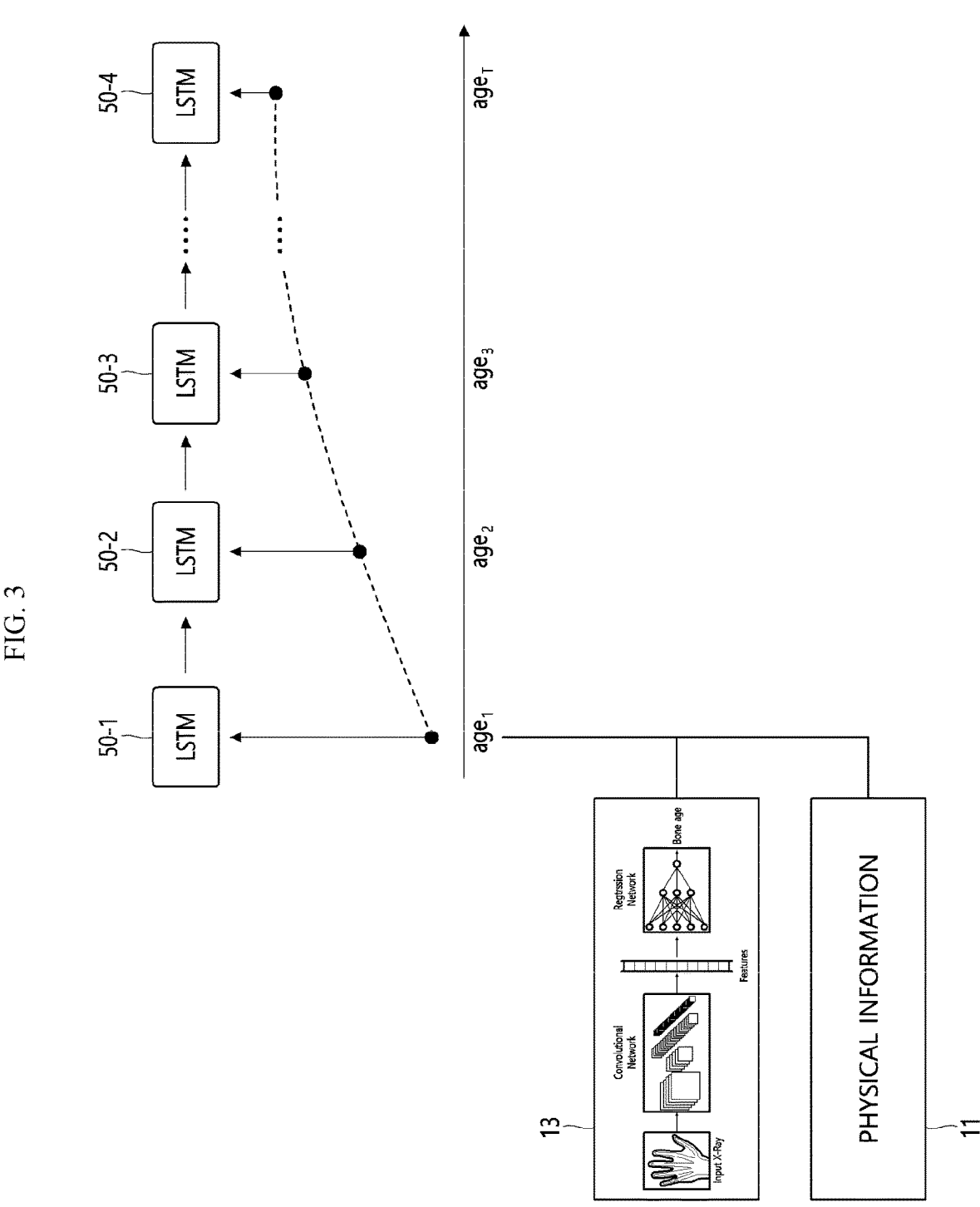
FIG. 3 is a diagram illustrating a configuration of a neural network for providing precocious puberty and solution for a growth stage according to an exemplary embodiment of the present invention.
Figure 4:
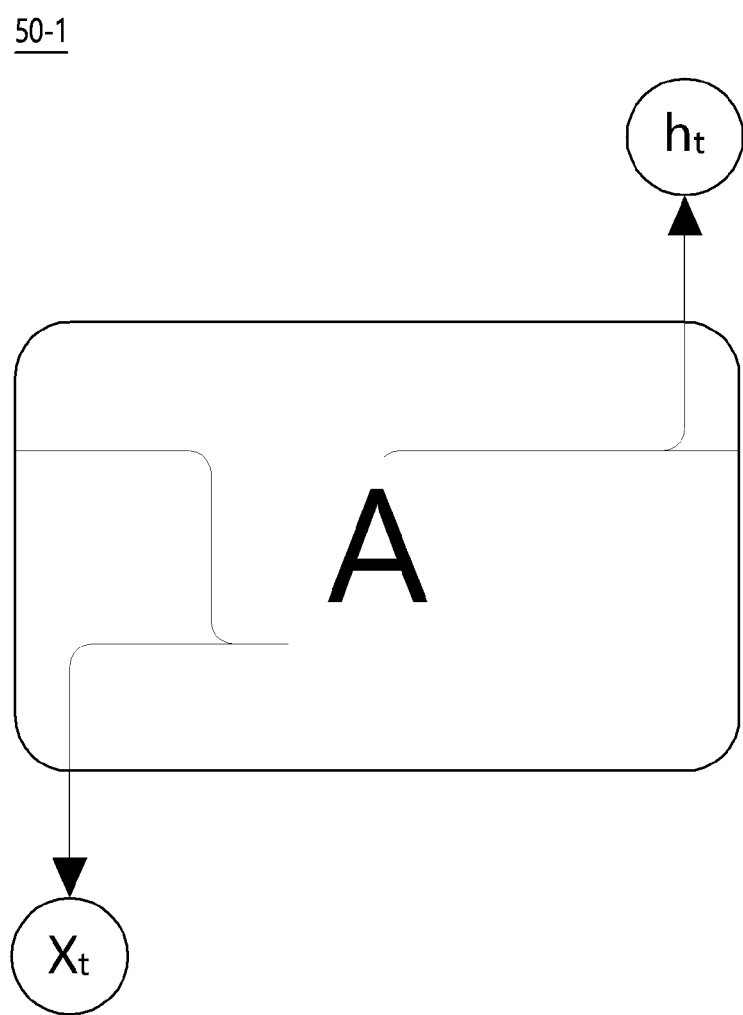
FIG. 4 is a diagram illustrating a first neural network model according to an exemplary embodiment of the present invention.
Figure 5:
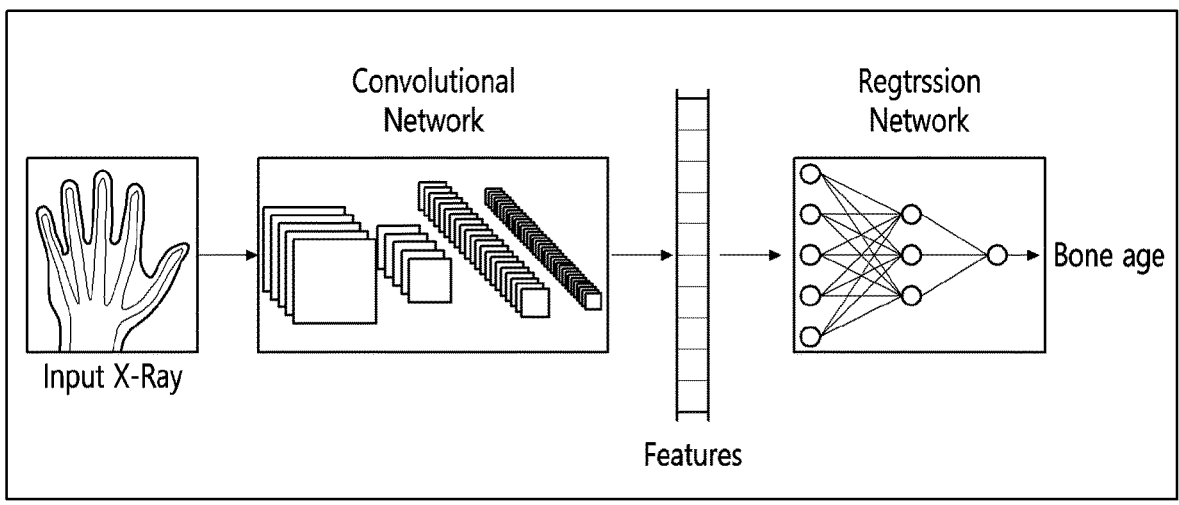
FIG. 5 is a diagram illustrating a second neural network model according to an exemplary embodiment of the present invention.

FIG. 3 is a diagram illustrating a configuration of a neural network that provides precocious puberty prediction and solution for each growth stage according to an exemplary embodiment of the present invention, FIG. 4 is a diagram illustrating a first neural network model according to an exemplary embodiment of the present invention, and FIG. 5 is a diagram illustrating a second neural network model according to an exemplary embodiment of the present invention.

It will be described with reference to FIGS. 3 to 5 below.

An exemplary embodiment of the present invention may include a first model 50 and a second model 13, and a pipeline may be built in which at least some of the output of the second model 13 is input to the first model 50.

More specifically, the first model 50 is a model that trains the physical information corresponding to at least one of the plurality of growth stages as training data based on time series physical information about a plurality of sample subjects. In the growth stage, the normal growth period 301, which is the time when the precocious puberty develops, may be adopted, but as described above, any one or more of the plurality of growth stages may be adopted to more accurately predict the precocious puberty.

The first model 50 includes an LSTM neural network 50 for training time series data, and trains the LSTM neural network 50 using past physical information on a plurality of sample subjects. Then, the current physical information on the evaluation subject 11 is input to the trained LSTM neural network 50 and the predicted growth rates for each growth stage are output.

The LSTM neural network 50 is trained using at least one of the physical information on the plurality of sample subjects as a default value. For example, for height, training is performed with annual height data during an arbitrary period or specific growth stage, and the prediction for the next year is made and compared with actual data. By this comparison, the training set is trained as it moves into the future at random periods or in units of specific growth stages.

In addition, as described above, compared to girls, boys have a lower proportion of idiopathic where the precocious puberty occurs without a bad cause disease and have a higher probability of having a serious pathological cause, so boys may be trained with more weight compared to girls.

In addition, the LSTM neural network 50 may be trained for each growth stage. Therefore, the normal growth period 301, the rapid growth period 303, the decelerated growth period 305, and the non-growth period 307 may each be trained with the past physical information 11 of the corresponding growth stage.

Illustratively, in this embodiment, the time series physical information on the plurality of sample subjects is sequentially input as the training data according to age or arbitrary period, and the calculation result of the prediction value at the past point in time or growth rate may be transmitted to the growth rate prediction at the next age or arbitrary period.

Therefore, the LSTM neural network 50 may not only predicts the growth rate based on the current physical information 11, but also train the extent to which prediction results 50-1, 2, 3, 4 by various indicators affects the past affect the current growth rate prediction, so items that have a significant impact on the change in the growth rate depending on age or arbitrary period among the indicators may be extracted and reflected in the growth rate prediction.

In addition, for time series learning, it is necessary to secure the physical information on the plurality of sample subjects at regular intervals. However, as described above, it may be difficult to regularly obtain the physical information on the plurality of sample subjects depending on age or arbitrary period, so it can be used by removing outlier physical information or non-continuous physical information for each unit period and normalizing it in time.

Meanwhile, the second model 13 may derive bone maturity (age) from a carpal image using a convolution neural network trained with bone maturity data of an evaluation subject as training data.

More specifically, the convolutional neural network may include a plurality of convolution layers that creates a feature map for features in an image to be analyzed among the carpal images and a pooling layer where sub-sampling is performed between the plurality of convolutional layers to extract features at different levels for an area to be analyzed, may be inferred probabilistically through an activation function, or may derive the bone maturity through learning weight learning between nodes through regression analysis.

The bone maturity extracted through the second model 13 may be input to the LSTM neural network 50 along with at least part of the physical information on the evaluation subject 11 to increase the prediction accuracy of the growth rate of the evaluation subject, thereby further increasing the prediction accuracy of precocious puberty.

Figure 6:
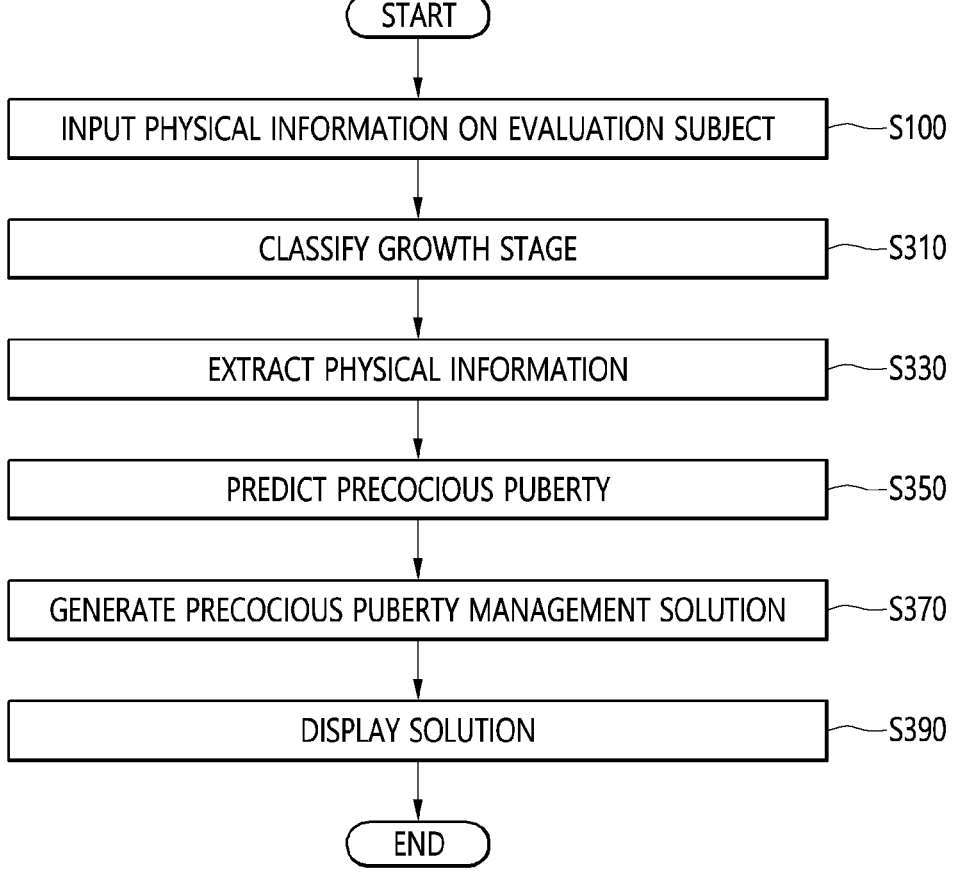
FIGS. 6 and 7 are flowcharts illustrating a method for providing precocious puberty prediction and solution for each growth stage using artificial intelligence according to various embodiments of the present invention.
Figure 7:
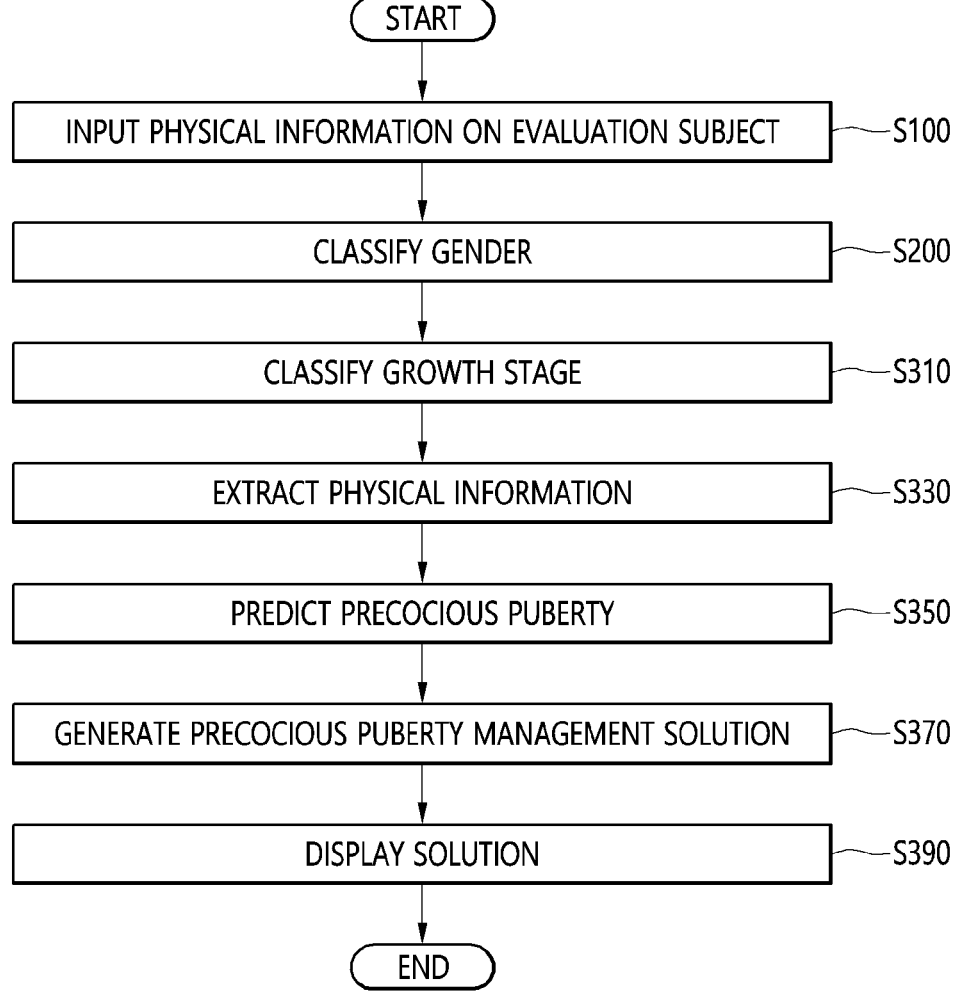

FIGS. 6 and 7 are flowcharts illustrating a method for providing growth prediction and solution for each growth stage using artificial intelligence according to various embodiments of the present invention.

It will be described with reference to FIGS. 1, 6, and 7 below.

When the physical information on the evaluation subject is input (S100) through the input unit 10, the growth stage classification unit 31 of the growth stage determination unit 30 may perform the classification into one of the plurality of growth stages based on the input physical information on the evaluation subject (S310), and the physical information extraction unit 33 may extract the physical information on the evaluation subject corresponding to the classified growth stage (S330).

More specifically, for accurate prediction of precocious puberty, the physical information extraction unit 33 may extract the physical information corresponding to the normal growth period 301 among the plurality of growth stages classified by the growth stage classification unit 31.

The prediction unit 50 may predict the growth rate based on the extracted physical information (S350). As described above, in the step (S350) of predicting the growth rate, it may be constructed to include a plurality of models that train individually extracted physical information on the plurality of growth stages as the training data based on the time series physical information on the plurality of sample subjects, so the solution generation unit 70 may generate the precocious puberty management solution based on the classified growth stage (S370). The generated precocious puberty management solution (S370) may be displayed to the evaluation subject through the display unit 90.

Meanwhile, as described above, since the classification standard for the growth stage may vary depending on the gender of the sample subject at each growth stage, an exemplary embodiment of the present invention may further include a step (S200) of receiving the physical information on the evaluation subject (S100) and then classifying the gender of the evaluation subject based on the physical information input through the gender determination unit 20.

Hereinabove, the present invention has been described with reference to exemplary embodiments. All exemplary embodiments and conditional illustrations disclosed in the present invention have been described to intend to assist in the understanding of the principle and the concept of the present invention by those skilled in the art to which the present invention pertains. Therefore, it will be understood by those skilled in the art to which the present invention pertains that the present invention may be implemented in modified forms without departing from the spirit and scope of the present invention.

Therefore, exemplary embodiments disclosed herein should be considered in an illustrative aspect rather than a restrictive aspect. The scope of the present invention should be defined by the claims rather than the above-mentioned description, and equivalents to the claims should be interpreted to fall within the present invention.

Meanwhile, the methods according to various exemplary embodiments of the present invention described above may be implemented as programs and be provided to servers or devices. Therefore, the respective apparatuses may access the servers or the devices in which the programs are stored to download the programs.

In addition, the methods according to various exemplary embodiments of the present invention described above may be implemented as programs and be provided in a state in which it is stored in various non-transitory computer-readable media. The non-transitory computer-readable medium is not a medium that stores data therein for a while, such as a register, a cache, a memory, or the like, but means a medium that semi-permanently stores data therein and is readable by an apparatus. In detail, the various applications or programs described above may be stored and provided in the non-transitory computer readable medium such as a compact disk (CD), a digital versatile disk (DVD), a hard disk, a Blu-ray disk, a universal serial bus (USB), a memory card, a read only memory (ROM), or the like.

Although the exemplary embodiments of the present invention have been illustrated and described hereinabove, the present invention is not limited to the specific exemplary embodiments described above, but may be variously modified by those skilled in the art to which the present invention pertains without departing from the scope and spirit of the invention as claimed in the claims. These modifications should also be understood to fall within the technical spirit and scope of the present invention.

DESCRIPTION OF REFERENCE NUMERALS

10: Input unit
20: Gender determination unit
30: Growth stage determination unit
50: Prediction unit
70: Solution generation unit
90: Display unit

The invention claimed is:

1. A method for providing precocious puberty prediction and solution for each growth stage using artificial intelligence, the method being performed by one or more processors of a computer system and comprising:

receiving time series physical information on an evaluation subject;

classifying, by a growth stage determination module executed on the computer system, a plurality of growth stages based on the input physical information on the evaluation subject, and then extracting physical information corresponding to a normal growth stage among the plurality of growth stages;

predicting precocious puberty by inputting the extracted physical information corresponding to the normal growth stage and an estimated bone maturity value generated by a bone maturity prediction model to a trained neural network stored in a memory and executed on the computer system, the trained neural network including a first neural network model trained with normal growth stage time-series physical information and a second neural network model trained with bone maturity data, such that an output of the second neural network model is provided as an input to the first neural network model; and providing a precocious puberty management solution based on the physical information on the evaluation subject when the evaluation subject corresponds to the precocious puberty, wherein the predicting comprises considering a difference between physical information of the evaluation subject and physical information corresponding to a normal growth stage so as to improve prediction accuracy for precocious puberty, wherein the precocious puberty management solution is determined differently for each of the plurality of growth stages based on the physical information on the evaluation subject, wherein the precocious puberty management solution is output through a user interface, wherein the method accurately predicts the precocious puberty by considering the plurality of growth stages of the evaluation subject through the neural network generated through artificial intelligence learning and provides solutions necessary to prevent the precocious puberty based on the accurate growth stage of the evaluation subject, wherein the predicting and providing are performed through a computer-implemented multi-model inference pipeline configured to improve computational accuracy and processing efficiency of the computer system, and wherein the second neural network model derives bone maturity from a carpal image using a convolutional neural network trained with the bone maturity data of the evaluation subject as training data, and the convolutional neural network includes a plurality of convolution layers that creates a feature map for features in an image to be analyzed among carpal images.

2. The method of claim 1, further comprising after the receiving of the physical information on the evaluation subject, classifying a gender of the evaluation subject.

3. The method of claim 2, wherein a period of the normal growth stage is set differently based on the gender of the evaluation subject to extract physical information.

4. The method of claim 1, wherein the neural network performs multi-modal learning using different types of training data.

5. The met hod of claim 4, wherein the neural network includes a first model that trains physical information corresponding to a normal growth stage among a plurality of growth stages as training data based on the time series physical information on the plurality of sample subjects.

6. The method of claim 5, wherein the neural network further includes a second model trained using bone maturity data of the evaluation subject as the training data.

7. A program stored in a computer-readable recording medium including a program code for executing the method for providing precocious puberty prediction and solution for each growth stage using artificial intelligence of claim 1.

8. A computer-readable recording medium in which a program for executing the method for providing precocious puberty prediction and solution for each growth stage using artificial intelligence of claim 1 is recorded.

9. A computer-implemented apparatus for providing precocious puberty prediction and solution for each growth stage using artificial intelligence, the apparatus comprising:

an input unit operable by one or more processors and configured to receive time series physical information on an evaluation subject;

a growth stage determination unit implemented using hardware and software components, and configured to classify a plurality of growth stages based on the physical information on the evaluation subject input to the input unit, and then extract physical information corresponding to a normal growth stage among the plurality of growth stages;

a precocious puberty prediction unit configured to predict the precocious puberty by inputting the extracted physical information corresponding to the normal growth stage and an estimated bone maturity value generated by a bone maturity prediction model to a trained neural network model stored in memory and executed on the apparatus, the trained neural network model including a first neural network model trained with normal growth stage time-series physical information and a second neural network model trained with bone maturity data, such that an output of the second neural network model is provided as an input to the first neural network model;

a solution generation unit configured to generate a precocious puberty management solution based on the physical information on the evaluation subject when the evaluation subject corresponds to the precocious puberty; and a display unit configured to display the generated precocious puberty management solution to a user interface, wherein the prediction unit is configured to consider a difference between physical information of the evaluation subject and physical information corresponding to a normal growth stage so as to improve prediction accuracy for precocious puberty, wherein the solution generation unit is configured to determine the precocious puberty management solution differently for each of the plurality of growth stages based on the physical information on the evaluation subject, wherein the apparatus is configured to implement a computer-implemented multi-model inference pipeline configured to improve computational accuracy and processing efficiency of the apparatus, and wherein the second neural network model derives bone maturity from a carpal image using a convolutional neural network trained with the bone maturity data of the evaluation subject as training data, and the convolutional neural network includes a plurality of convolution layers that creates a feature map for features in an image to be analyzed among carpal images.

10. The apparatus of claim 9, further comprising:

a gender determination unit configured to classify a gender of the evaluation subject input to the input unit, wherein the solution generation unit generates a precocious puberty management solution differently depending on the gender of the evaluation subject.

11. The apparatus of claim 10, wherein the growth stage determination unit extracts the physical information by setting a period of the normal growth stage differently based on the gender of the evaluation subject.

12. The apparatus of claim 9, wherein the neural network performs multi-modal learning using different types of training data.

13. The apparatus of claim 12, wherein the neural network includes a first model that trains physical information corresponding to a normal growth stage among a plurality of growth stages as training data based on the time series physical information on the plurality of sample subjects.

14. The apparatus of claim 13, wherein the neural network further includes a second model trained using bone maturity data of the evaluation subject as the training data.

* * * * *